United States Patent [19]

Wright

[11] Patent Number: 5,662,957
[45] Date of Patent: Sep. 2, 1997

[54] OIL CONTAINING LIPID VESICLES WITH MARINE APPLICATIONS

[75] Inventor: D. Craig Wright, Gaithersburg, Md.

[73] Assignee: Novavax, Inc., Columbia, Md.

[21] Appl. No.: 643,171

[22] Filed: May 3, 1996

[51] Int. Cl.$^6$ .............. A23D 7/005; A23K 1/18; A61K 9/127
[52] U.S. Cl. .......... 426/605; 426/612; 426/613; 424/442; 424/450; 514/938
[58] Field of Search ................ 426/601, 602, 426/604, 605, 612, 613; 424/442, 450; 514/938, 939, 941; 436/829

[56] References Cited

U.S. PATENT DOCUMENTS

| | | | |
|---|---|---|---|
| 2,216,485 | 10/1940 | Brandt | 426/602 |
| 4,861,610 | 8/1989 | Kato et al. | 426/602 |
| 4,895,452 | 1/1990 | Yiournas et al. | 366/173 |
| 4,911,928 | 3/1990 | Wallach | 424/450 |
| 4,966,779 | 10/1990 | Kirk | 426/602 |
| 4,971,826 | 11/1990 | Kato et al. | 426/602 |
| 5,080,921 | 1/1992 | Reimer | 426/602 |
| 5,192,577 | 3/1993 | Masson | 426/602 |
| 5,234,767 | 8/1993 | Wallach | 428/402.2 |
| 5,256,422 | 10/1993 | Albert et al. | 426/602 |
| 5,322,704 | 6/1994 | Gaonkar | 426/601 |
| 5,376,397 | 12/1994 | Gaonkar | 426/602 |
| 5,474,848 | 12/1995 | Wallach | 424/450 |

*Primary Examiner*—Thomas B. Wyse
*Attorney, Agent, or Firm*—Lahive & Cockfield, LLP

[57] ABSTRACT

Disclosed is a new class of lipid vesicles, liposoils, which have high oil content, low water content, and protein. The liposoils are made using a combination of a surfactant and either dried egg yolk or dried whole egg as the wall material, oil, and an aqueous diluent. Unlike most lipid vesicles, the liposoils can be made with an aqueous diluent having high salinity; in fact, sea water is a preferred aqueous diluent. Liposoils have particular applicability as a food for marine environments, such as a food source for filter feeders such as oysters. Methods of making the liposoils is also disclosed.

21 Claims, No Drawings

OIL CONTAINING LIPID VESICLES WITH MARINE APPLICATIONS

BACKGROUND OF THE INVENTION

The present invention is concerned with the materials and methods for constructing a new type of lipid vesicle, called a "liposoil". Liposoils are micron-sized vesicles containing oil, dried egg, surfactant and a diluent. The diluent can vary in salinity from water suitable for injection to solutions with the salinity of seawater. Liposoils are produced using high shear force without the use of organic solvents and are freely suspendable in water. The diluent or water content of these structures is low, normally 20-40% on a volume per volume basis. Since all materials utilized in the construction of liposoils are food grade, USP or NF grade materials, liposoils are suitable for human and animal enteral use applications. Liposoils are stable at temperatures from 4° to 37° C. and are not degraded by exposure to strong acids and base. Due to the ability to use high salinity diluents in formation of these structures these materials have potential marine applications, particularly as a marine food. The size and the fact that they are constructed of edible materials allows filtration and metabolism of these structures by marine filter feeders. The liposoils have a high protein content from the dried egg used in their formation, which is also adventageous in their use aqs a marine food.

Liposoils differ from classic liposomes in several ways. Classic liposomes were constructed of phospholipids such as phosphatidylcholine or lecithin extracted from a variety of sources (including eggs) but dried whole egg or egg yolk was not used as a wall material. Both egg yolk and whole egg have a high protein content in addition to the lipid content. Classic liposomes do not have this high protein content, and, in fact, the protein which can be encapsulated may be limited. This limitation is not found in liposoils. In addition, only small amounts of oil, compared to large amounts of oil used in liposoils, could be incorporated before the liposome broke down. Still another difference between the classic liposomes and the liposoils is the ability to use high saline solutions in the manufacture of liposoils. High saline solutions prevented the formation of the classic liposomes.

The method of manufacturing liposoils is also different than that used in classical liposome formation. Classical liposomes are normally formed utilizing the Bangham method, or a variant thereof. In the Bangham method, the lipids are dissolved in organic solvent, the solvent is removed to form a film, and the film is rehydrated with an aqueous solution to form liposomes. Organic solvents are not needed to make liposoils and, in fact, may impede the formation process.

Although some workers in the lipid vesicle field have used procedures other than Bangham method, and materials other than classic phospholipids, there is little work on vesicles made using both phospholipids and surfactants in the vesicle walls. For example, although U.S. Pat. No. 5,234,767, entitled "Hybrid Paucilamellar Lipid Vesicles", the disclosure of which is incorporated herein by reference, discusses vesicles which may have a phospholipid and nonphospholipid in the vesicle wall, the phospholipids discussed are purified phosphatidylcholine and the like, not crude dried egg yolk or dried egg. These materials do not have the high protein content of the liposoils of the present invention. In addition, there is no discussion in this patent of using high salinity diluents nor that less water could be used than lipid.

The ability of the liposoils to have high oil content and be made using high salinity diluents such as sea water leads to an optimum usage in the marine environment, particularly in the marine food environment. Little or no work has been done in this field using liposomes because of the stability problems in this high salinity environment. The liposoils of the present invention are much better suited to this environment than classic liposomes or even most lipid vesicles using nonphospholipid materials. In addition, most non-phospholipid materials used to make lipid vesicles are not food grade or safe for incorporation into the food chain.

Accordingly, an object of the invention is to provide a new type of lipid vesicle, the liposoil, which has high oil content, utilizes dried egg or egg yolk, and can be made in a high salinity environment.

A further object of the invention is to provide a method of making the liposoils of the invention.

A still further object of the invention is to provide a marine food and/or pharmaceutical which is useful in a high salinity environment.

These and other objects and features of the invention will be apparent from the following description and the claims.

SUMMARY OF THE INVENTION

The present invention features a method of forming a composition containing a new type of structure, designated herein as the liposoil, and the composition itself. This composition, which contains oil encapsulated in the liposoil lipid structure, is made by blending a surfactant selected from the group consisting of polyoxyethylene sorbitan fatty acid esters, sorbitan fatty acid esters, polyoxyethylene nonylphenyl ethers, octylphenoxy-polyethoxyethanols, and mixtures thereof with a wall-forming material and an excess of oil to form a lipid preblend. The wall-forming material is dried egg yolk solids or dried whole egg solids and the oil is preferably an edible oil, most preferably an oil selected from the group consisting of almond oil, apricot seed oil, canola oil, castor oil, coconut oil, cod liver oil, corn oil, cottonseed oil, menhaden oil, jojoba bean oil, linseed oil, macadamia nut oil, mineral oil, mink oil, olive oil, palm oil, peanut oil, safflower oil, sardine oil, sesame oil, squalene, sunflower seed oil, and wheat germ oil. This preblend is then blended with an aqueous diluent to form the liposoil composition, the lipid preblend being greater in volume than the aqueous diluent. While a variety of diluents can be used, preferred diluents have greater than physiologically normal saline content and may include natural or synthetic sea water. Preferred liposoil compositions are lipid structures less than 1.2 microns in diameter. These compositions may also include an oil or aqueous soluble therapeutic active agent. If an aqueous soluble agent is used, it is added to the aqueous diluent before blending with the lipid preblend, while if an oil soluble agent is used, it is added to the oil prior to the forming of the lipid preblend.

The compositions of the invention have particular utility as foods for marine animals, particularly marine filter feeders such as oysters and clams. Both egg yolk and dried whole egg have a high protein content, so the marine food made using liposoils provides needed dietary protein as well as lipid. These compositions can also contain a therapeutically active agent, e.g., an antibiotic, which could prevent some of the common illnesses of the filter feeders. By using the compositions of the invention as a food for these marine animals, more careful control may be had over their diet.

The following detailed description of the invention will further amplify particular uses and methods of manufacture for the composition of the invention.

DETAILED DESCRIPTION OF THE INVENTION

The lipid structures of the present invention (designated herein liposoils) provide inherently different properties than classic liposomes or other lipid structures. These structures combine the stability of lipid vesicles with high oil content and high salinity from the aqueous diluent which allows them to be used in environments which are detrimental to the stability of classic lipid vesicles. In addition, these vesicles should not be as susceptible to problems such as the donnan effect as are other vesicles. Accordingly, they may be used in harsher environmental conditions.

The following examples more clearly illustrate how the liposoils are made and their properties. These examples are purely illustrative and are not intended to limit the invention.

EXAMPLE 1

In this example, the preferred materials for making the liposoils, and their methods of preparation, are described. For preparation of the liposoils, at least one oil from Table 1 is combined with a surfactant from Table 2 and a wall-forming material from Table 3. After premixing these materials, water or a suitable diluent from Table 4 is injected into this mixture. The preferred ratio of oil:surfactant:wall material in the pre-mixed materials is 25:3:1 on a volume/volume/weight basis. The preferred ratios of the pre-mixed materials to water is 4:1 (20% diluent) or 3:2 (40% diluent). Liposoils can be produced with reciprocating syringe instrumentation, continuous flow instrumentation, or high speed mixing equipment. The mixers described in U.S. Pat. No. 4,895,452, entitled "Method and Apparatus for Producing Lipid Vesicles", the disclosure of which is incorporated herein by reference, can all be used. Other mixers, such as French presses or microfluidizers such as are described in U.S. Pat. No. 4,911,928, entitled "Paucilamellar Lipid Vesicles", the disclosure of which is incorporated herein by reference, can also be used. Particles created at this 3:2 ratio range in diameters from 44 to 1,197 nanometers.

TABLE 1

List of Oils Utilized in Preparation of Liposoils

Almond oil, sweet
Apricot seed oil
Canola oil
Castor oil
Coconut oil
Cod Liver oil
Corn oil
Cotton seed oil
Jojoba bean oil
Linseed oil, boiled
Macadamia nut oil
Medhaden Oil
Mineral oil
Mink oil
Olive oil
Palm oil
Peanut oil
Sardine Oil
Safflower oil
Sesame oil
Squalane
Sunflower seed oil
Wheat germ oil

TABLE 2

List of Surfactants Utilized in Preparation of Liposoils

Polyoxythylene Sorbitan Festers and Sorbitan Esters

Tween 20
Tween 40
Tween 60
Tween 80
Tween 85
Span 85
Nonylphenol Polyethylene Glycol Ethers
(alkylphenol-hydroxypolyoxyethylene)

Poly(oxy-1,2-ethaneolyl),alpha-(4-nonylphenal)-omega-hydroy-, branched
(i.e., Tergitol NP-6 Surfactant)
Poly(oxy-1,2-ethaneolyl),alpha-(4-nonylphenal)-omega-hydroy-, branched
(i.e., Tergitol NP-7 Surfactant)
Poly(oxy-1,2-ethaneolyl),alpha-(4-nonylphenal)-omega-hydroy-, branched
(i.e., Tergitol NP-8 Surfactant)
Poly(oxy-1,2-ethaneolyl),alpha-(4-nonylphenal)-omega-hydroy-, branched
(i.e., Tergitol NP-9 Surfactant)
Poly(oxy-1,2-ethaneolyl),alpha-(4-nonylphenal)-omega-hydroy-, branched
(i.e., Tergitol NP-12 Surfactant)
Nonylphenol Polyethylene Glycol Ether mixtures
(ie. Tergital NP-70 (70% AQ) Surfactant)
Octylphenoxypolyethosyethanols

| | |
|---|---|
| Triton | X-15 |
| Triton | X-100 |
| Triton | X-102 |
| Triton | X-114 |

TABLE 3

List of Wall Materials Utilized in Preparation of Liposoils.

Dried whole egg
Dried egg yolk

TABLE 4

List of Diluents Utilized in Preparation of Liposoils.

Water for injection
Phosphate buffered saline
Seawater

By varying these components, custom liposoils can be formed.

EXAMPLE 2

In this Example, various specific liposoil formulations are described. Table 5 lists the materials utilized to produce one formulation of liposoils utilizing water as the diluent and their sizing parameters on Coulter LS230 laser sizing apparatus (Table 6). A brief description of the method of production of the liposoils is also given.

TABLE 5

Preparation of Liposoils Utilizing Water as the Diluent.

| Chemical Component | Amount |
|---|---|
| Soybean oil (Oil) | 25 mL |
| Polysorbate 80 (Tween 80) (Surfactant) | 3 mL |
| Dried egg (Wall material) | 1 g |

The oil-surfactant-wall material components are mixed for 60 seconds. Two mL of water is injected into three mL of the mixture using reciprocating syringe instrumentation.

TABLE 6

| Preparation | LS-230 Mean Diameter (nanometers) | LS-230 Range (nanometers) |
|---|---|---|
| Liposoils (SBO/Tw8O/Dried whole egg/ WFI) | 583 | 326–945 |

Table 7 lists the materials utilized to produce a different formulation of liposoils utilizing phosphate buffered saline as the diluent. Sizing data on this preparation from a Coulter LS230 laser sizing apparatus follows in Table 8.

TABLE 7

Preparation of Liposoils Utilizing Phosphate Buffered Saline as the Diluent.

| Chemical Component | Amount |
|---|---|
| Soybean oil (Oil) | 25 mL |
| Polysorbate 80 (Tween 80) (Surfactant) | 3 mL |
| Dried whole egg (Wall material) | 1 g |

As mentioned above, the oil-surfactant-wall material components are mixed for 60 seconds to form a lipid preblend. Two mL of PBS is injected into three mL of the mixture using reciprocating syringe instrumentation. Table 8 shows the sizing parameters for the liposoils obtained with these materials.

TABLE 8

| Preparation | LS-230 Mean Diameter (nanometers) | LS-230 Range (nanometers) |
|---|---|---|
| Liposoils (SBO/Tw8O/Dried whole egg/ PBS) | 563 | 313–917 |

Table 9 lists the materials utilized to produce still another formulation of liposoils utilizing seawater as the diluent. Sizing data on this preparation from a Coulter LS230 laser sizing apparatus follows in Table 10.

TABLE 9

Preparation of Liposoils Utilizing Seawater as the Diluent.

| Chemical Component | Amount |
|---|---|
| Soybean oil (Oil) | 25 mL |
| Polysorbate 80 (Tween 80) (Surfactant) | 3 mL |
| Dried egg (Wall material) | 1 g |

The oil-surfactant-wall material components are mixed for 60 seconds to form the lipid preblend. Two mL of seawater is injected into three mL of the mixture using reciprocating syringe instrumentation. Table 10 shows sizing data for this formulation.

TABLE 10

| Preparation | LS-230 Mean Diameter (nanometers) | LS-230 Range (nanometers) |
|---|---|---|
| Liposoils (SBO/Tw8O/Dried whole egg/ seawater) | 558 | 323–883 |

EXAMPLE 3

In Example 2, whole dried egg was used as the wall material. In this example, dried egg yolk is used instead. Table 11 lists the materials utilized to produce liposoils utilizing dried egg yolk instead of whole dried egg and Table 12 shows their sizing parameters on Coulter LS230 Laser sizing apparatus.

TABLE 11

Preparation of Liposoils Utilizing Water as the Diluent and Dried Egg Yolk.

| Chemical Component | Amount |
|---|---|
| Soybean oil (Oil) | 25 mL |
| Polysorbate 80 (Tween 80) (Surfactant) | 3 mL |
| Dried egg yolk (Wall material) | 1 g |

The oil-surfactant-wall material components are mixed for 60 seconds. Two mL of water is injected into three mL of the mixture using reciprocating syringe instrumentation. The resulting liposoils were then sized using the laser sizing device.

TABLE 12

| Preparation | LS-230 Mean Diameter (nanometers) | LS-230 Range (nanometers) |
|---|---|---|
| Liposoils (SBO/Tw8O/Dried egg yolk/ WFI) | 380 | 203–577 |

As in Example 2, various diluents were used in the preparation of different formulations of the liposoils. Table 13 lists the materials utilized to produce liposoils utilizing phosphate buffered saline as the diluent and dried egg yolk instead of whole dried egg. Sizing data on this preparation from a Coulter LS230 laser sizing apparatus follows in Table 14.

TABLE 13

Preparation of Liposoils Utilizing Phosphate Buffered Saline as the Diluent and Dried Egg Yolk.

| Chemical Component | Amount |
|---|---|
| Soybean oil (Oil) | 25 mL |
| Polysorbate 80 (Tween 80) (Surfactant) | 3 mL |
| Dried egg yolk (Wall material) | 1 g |

The oil-surfactant-wall material components are mixed for 60 seconds. Two mL of saline is injected into three mL of the mixture using reciprocating syringe instrumentation. Table 14 shows the sizes of the resulting liposoils.

TABLE 14

| Preparation | LS-230 Mean Diameter (nanometers) | LS-230 Range (nanometers) |
| --- | --- | --- |
| Liposoils (SBO/Tw80/Dried egg yolk/ PBS) | 608 | 349–974 |

Table 15 lists the materials utilized to produce liposoils utilizing seawater as the diluent and dried egg yolk instead of whole dried egg. Sizing data on this preparation from a Coulter LS230 laser sizing apparatus follows in Table 16.

TABLE 15

Preparation of Liposoils Utilizing Seawater as the Diluent and Dried Egg Yolk.

| Chemical Component | Amount |
| --- | --- |
| Soybean oil (Oil) | 25 mL |
| Polysorbate 80 (Tween 80) (Surfactant) | 3 mL |
| Dried egg yolk (Wall material) | 1 g |

The oil-surfactant-wall material components are mixed for 60 seconds. Two mL of seawater is injected into three mL of the mixture using reciprocating syringe instrumentation. Table 16 shows the sizing data.

TABLE 16

| Preparation | LS-230 Mean Diameter (nanometers) | LS-230 Range (nanometers) |
| --- | --- | --- |
| Liposoils (SBO/Tw8O/Dried whole egg/ seawater) | 589 | 331–949 |

EXAMPLE 4

In this Example, the type of oil used was varied to produce different liposoil formulations. Table 17 lists the materials utilized to produce liposoils where the oil component is varied utilizing seawater as the diluent. The volume of each oil utilized was 25 mL. The volume of surfactant (Tween 80) was 3 mL. The weight of the wall material utilized was 1 gram. In each preparation, the oil-surfactant-wall material components were mixed for 60 seconds. Two mL of seawater is injected into three mL of the mixture using reciprocating syringe instrumentation. Sizing information was determined on each preparation on a Coulter LS230 laser sizing apparatus and is shown on Table 17.

TABLE 17

Preparation of Liposoils Containing Tween 80 and Dried Whole Egg, varying the Oil and Utilizing Seawater as the Diluent.

| Chemical Component | LS-230 Mean Diameter (nanometers) | LS-230 Range (nanometers) |
| --- | --- | --- |
| Almond oil, sweet | 656 | 359–1,086 |
| Apricot seed oil | 654 | 343–1,119 |
| Canola oil | 465 | 240–747 |
| Castor oil | 508 | 308–716 |
| Coconut oil | 563 | 268–1,073 |
| Cod Liver oil | 683 | 384–1,111 |
| Corn oil | 647 | 401–972 |
| Cotton seed oil | 637 | 336–1086 |
| Fish oil | 610 | 381–911 |
| Jojoba bean oil | 673 | 342–1,197 |
| Linseed oil, boiled | 585 | 394–814 |
| Macadamia nut oil | 666 | 378–1,082 |
| Mineral Oil | 509 | 272–812 |
| Mink oil | 645 | 347–1,090 |
| Olive oil | 663 | 380–1,062 |
| Palm oil | 604 | 421–829 |
| Peanut oil | 684 | 366–1,164 |
| Safflower oil | 665 | 380–1,067 |
| Sesame oil | 680 | 361–1,161 |
| Squalane | 549 | 281–956 |
| Squalene (batch 2) | 686 | 413–1,060 |
| Sunflower seed oil | 638 | 322–1,152 |
| Wheat germ oil | 638 | 380–985 |

EXAMPLE 5

This Example illustrates various surfactants useful in formulating liposoils. Table 18 lists the materials utilized to produce liposoils where the surfactant component is varied utilizing seawater as the diluent, including sizing data. The volume of soybean oil utilized was 25 mL. The volume of surfactant was 3 mL. The weight of the wall material (dried whole egg) utilized was 1 gram. In each preparation, the oil-surfactant-wall material components were mixed for 60 seconds. Two mL of seawater is injected into three mL of the mixture using reciprocating syringe instrumentation. Sizing information was determined on each preparation on a Coulter LS230 laser sizing apparatus and is shown in Table 18.

TABLE 18

Preparation of Liposoils Containing Soybean Oil and Dried Whole Egg, Varying the Surfactant and Utilizing Seawater as the Diluent.

| Chemical Component | LS-230 Mean Diameter (nanometers) | LS-230 Range (nanometers) |
| --- | --- | --- |
| Sorbitan Derivatives | | |
| Tween 20 | 592 | 329–964 |
| Tween 40 | 606 | 375–915 |
| Tween 60 | 571 | 387–798 |
| Tween 80 | 589 | 331–949 |
| Tween 85 | 539 | 339–790 |
| Span 85 | 363 | 200–544 |
| Nonlyphenol Polyethylene Glycol Ethers | | |
| Tergitol MP-6 Surfactant | 512 | 315–721 |
| Tergitol NP-7 Surfactant | 468 | 290–674 |
| Tergitol NP-8 Surfactant | 481 | 291–702 |
| Tergitol NP-9 Surfactant | 376 | 222–552 |
| Tergitol NP-12 Surfactant | 382 | 225–561 |

TABLE 18-continued

Preparation of Liposoils Containing Soybean Oil and Dried Whole Egg, Varying the Surfactant and Utilizing Seawater as the Diluent.

| Chemical Component | LS-230 Mean Diameter (nanometers) | LS-230 Range (nanometers) |
|---|---|---|
| Tergitol NP-70 (70% AQ) Surfactant Octylphenoxypoly- ethoxyethanols | 78 | 45–125 |
| Triton X-15 | 77 | 44–122 |
| Triton X-100 | 555 | 386–760 |
| Triton X-102 | 325 | 168–502 |
| Triton X-114 | 557 | 349–810 |

EXAMPLE 6

In this Example, various physical stability tests were run on liposoils made as in Example 2 using seawater as the diluent.

Table 19 displays stability data on liposoils after exposure to strong acids and base. After two hour exposures of liposoils to either 1N sodium hydroxide, 1N sulfuric acid, or 1N nitric acid, no evidence of disruption of structures was noted.

TABLE 19 pH Stability of Liposoils after a Two Hour Exposure to Strong Base or Acids

| Preparation | LS-230 Mean Diameter (nanometers) | LS-230 Range (nanometers) |
|---|---|---|
| Liposoils (SBO/Tw8O/dried whole egg/seawater) (Initial Preparation) | 589 | 331–949 |
| Liposoils (SBO/Tw8O/dried whole egg/seawater) (2 hour exposure to 1N NaOH) | 503 | 286–787 |
| Liposoils (SBO/Tw8O/dried whole egg/seawater) (2 hour exposure to 1N $H_2SO_4$) | 512 | 287–819 |
| Liposoils (SBO/Tw8O/dried whole egg/seawater) (2 hour exposure to IN $HNO_3$) | 533 | 299–851 |

Table 20 displays sizing information on liposoils stored at −20° C., 4° C., 25° C., 37° C. or 56° C. Liposoils were stable at 4° C., 25° C. and 37° C. but unstable at −20° C. and 56° C.

TABLE 20

Thermal Stability of Liposoils at One Month

| Preparation | LS-230 Mean Diameter (nanometers) | LS-230 Range (nanometers) |
|---|---|---|
| Liposoils (SBO/Tw80/dried whole egg/seawater) STORAGE at −20° C. | | Unstable |
| Liposoils (SBO/Tw80/dried whole egg/seawater) STORAGE at 4° C. | 381 | 204–584 |
| Liposoils (SBO/Tw80/dried whole egg/seawater) STORAGE at 25° C. | 275 | 142–427 |
| Liposoils (SBO/Tw80/dried whole egg/seawater) STORAGE at 37° C. | 269 | 138–420 |
| Liposoils (SBO/TW80/dried whole egg/seawater) STORAGE at 56° C. | | Unstable |

EXAMPLE 7

To determine whether liposoils could be used as a food for filter factors, liposoils made as in Example 2 using seawater as the diluent fed to eastern oysters free of *Perkinsus marinus* infection. The oysters were placed in 50 liter aerated polypropylene tanks, twelve oysters per tank and acclimated for two weeks. Water was changed every other day with estuarine water prefiltered through a series of ten micron and one micron filters. Oysters were fed daily with 0.1 g of algeal paste of *Thalassiosira weisfolggi* resuspended in water. After two weeks of acclamation, 50 mL of liposoils was added to each tank. This amount of material caused marked tank turbidity. All material was filtered out of estuarine water by the oysters in three hours.

Oysters can be grown by substitution of liposoils for standard commercial oyster food. The liposoils provide not just lipid but also high protein content from the dried egg or dried egg yolk. This protein is an important part of the feed for the marine filter feeders. In addition, a test using an antibiotic bacitracin, which was included in the lipid preblend before the formation of the liposoils, showed that the oysters tolerated the antibiotic-liposoil combination well. Liposoils have the potential for being used as both marine foods and therapeutic delivery systems.

The foregoing examples are non-limiting and are set forth merely to elucidate the invention. The invention is defined by the following claims.

What is claimed is:

1. A method of forming a composition containing oil encapsulated in a lipid structure comprising the steps of:

blending a surfactant with a wall-forming material and an excess of oil to form a lipid pre-blend, said surfactant being selected from the group consisting of polyoxyethylene sorbitan fatty acid esters, sorbitan fatty acid esters, polyoxyethylene nonylphenyl ethers, octylphenoxypolyethoxyethanols, and mixtures thereof; and said wall-forming material being selected from the group consisting of egg yolk solids and whole egg solids; and blending said lipid pre-blend with an aqueous based diluent to form said composition, said lipid pre-blend being greater in volume than said aqueous diluent, said composition having said oil encapsulated in said lipid structure.

2. The method of claim 1 wherein said aqueous diluent consists essentially of a solution which has greater than physiologically normal saline content.

3. The method of claim 2 wherein said aqueous diluent comprises natural or synthetic sea water.

4. The method of claim 1 wherein said oil is selected from the group consisting of almond oil, apricot seed oil, canola oil, castor oil, coconut oil, cod liver oil, corn oil, cotton seed oil, manhattan oil, jojoba bean oil, linseed oil, macadamia nut oil, mineral oil, mink oil, olive oil, palm oil, peanut oil, safflower oil, sardine oil, sesame oil, squalane, sunflower seed oil, and wheat germ oil.

5. The method of claim 1 wherein said blending of said lipid pre-blend and said aqueous diluent is sufficient such that said lipid structures formed are less than 1.2 microns in diameter.

6. The method of claim 1 wherein said composition further comprises an oil-soluble therapeutic active agent, said active agent being added to said lipid pre-blend before blending with aqueous diluent.

7. The method of claim 1 wherein said composition further comprises an aqueous-soluble therapeutic active agent, said active agent being added to said aqueous diluent before blending with lipid pre-blend.

8. A food for marine filter feeders comprising a lipid structure encapsulating an oil, said lipid structure being formed of a surfactant, a wall-forming material, an excess of oil, and an aqueous diluent, said surfactant being selected from the group consisting of polyoxyethylene sorbitan fatty acid esters, sorbitan fatty acid esters, polyoxyethylene nonylphenyl ethers, octylphenoxypolyethoxyethanols, and mixtures thereof; and said wall-forming material being selected from the group consisting of egg yolk solids and whole egg solids.

9. The food of claim 8 wherein said aqueous diluent consists essentially of a solution which has greater than physiologically normal saline content.

10. The food of claim 9 wherein said aqueous diluent comprises natural or synthetic sea water.

11. The food of claim 8 wherein said oil is selected from the group consisting of almond oil, apricot seed oil, canola oil, castor oil, coconut oil, cod liver oil, corn oil, cotton seed oil, fish oil, jojoba bean oil, linseed oil, macadamia nut oil, mineral oil, mink oil, olive oil, palm oil, peanut oil, safflower oil, sesame oil, squalane, sunflower seed oil, and wheat germ oil.

12. The food of claim 8 wherein said lipid structures are less than 1.2 microns in diameter.

13. The food of claim 8 wherein said food further comprises an oil-soluble therapeutic active agent.

14. The food of claim 8 wherein said food further comprises an aqueous-soluble therapeutic active agent.

15. A lipid structure comprising a surfactant selected from the group consisting of polyoxyethylene sorbitan fatty acid esters, sorbitan fatty acid esters, polyoxyethylene nonylphenyl ethers, octylphenoxypolyethoxyethanols, and mixtures thereof; a wall-forming material selected from the group consisting of egg yolk solids and whole egg solids; an oil; and an aqueous based diluent, the combined amounts of said surfactant, wall material and oil being greater in volume than said aqueous diluent.

16. The lipid structure of claim 15 wherein said aqueous diluent consists essentially of a solution which has greater than physiologically normal saline content.

17. The lipid structure of claim 16 wherein said aqueous diluent comprises natural or synthetic sea water.

18. The lipid structure of claim 15 wherein said oil is selected from the group consisting of almond oil, apricot seed oil, canola oil, castor oil, coconut oil, cod liver oil, corn oil, cotton seed oil, fish oil, jojoba bean oil, linseed oil, macadamia nut oil, mineral oil, mink oil, olive oil, palm oil, peanut oil, safflower oil, sesame oil, squalane, sunflower seed oil, and wheat germ oil.

19. The lipid structure of claim 15 wherein said lipid structures are less than 1.2 microns in diameter.

20. The lipid structure of claim 15 wherein said lipid structure further comprises an oil-soluble therapeutic active agent.

21. The lipid structure of claim 15 wherein said lipid structure further comprises an aqueous-soluble therapeutic active agent.

* * * * *